United States Patent [19]

Schubert

[11] Patent Number: 5,132,483

[45] Date of Patent: Jul. 21, 1992

[54] PROCESS TO REDUCE FINES PRODUCED DURING THE CATALYTIC DIMERIZATION OF OLEFINS

[75] Inventor: Paul F. Schubert, Campbell, Calif.

[73] Assignee: Phillips Petroleum Company, Bartlesville, Okla.

[21] Appl. No.: 765,793

[22] Filed: Sep. 26, 1991

[51] Int. Cl.$^5$ .......................... C07C 2/26; C07C 2/34
[52] U.S. Cl. .................... 585/511; 585/510; 585/516; 585/520; 585/530
[58] Field of Search ............... 585/510, 511, 516, 520, 585/530

[56] References Cited

U.S. PATENT DOCUMENTS

| | | | |
|---|---|---|---|
| 3,291,752 | 12/1966 | Hambling et al. | 585/516 |
| 3,624,177 | 11/1971 | Lowther | 585/516 |
| 3,689,587 | 9/1972 | Crebbell et al. | 585/329 |
| 3,950,450 | 4/1976 | Hashimoto et al. | 585/516 |
| 4,388,480 | 6/1983 | Imai et al. | 585/510 |
| 4,520,126 | 5/1985 | Kawamoto et al. | 502/184 |
| 4,656,154 | 4/1987 | Drake | 502/185 |
| 4,687,877 | 8/1987 | Bartley et al. | 502/345 |
| 4,774,215 | 9/1988 | Drake et al. | 502/174 |

FOREIGN PATENT DOCUMENTS 1163092  9/1969  United Kingdom.

Primary Examiner—Asok Pal
Assistant Examiner—E. D. Irzinski
Attorney, Agent, or Firm—Carl D. Corvin

[57] ABSTRACT

A process is provided which comprises: (a) contacting at least one olefinic compound with an alkali metal/alkali metal carbonate catalyst system at a temperature below the dimerization temperature range of the dimerization reaction; followed by (b) heating said olefin compound and said alkali metal carbonate catalyst system to a temperature in said dimerization temperature range.

11 Claims, No Drawings

PROCESS TO REDUCE FINES PRODUCED DURING THE CATALYTIC DIMERIZATION OF OLEFINS

BACKGROUND OF THE INVENTION

This invention relates to dimerization processes.

Alkali metal/alkali metal carbonate catalytic systems are well known in the art an dare disclosed, for example, in U.S. Pat. Nos. 4,544,790; 4,609,637; and 4,656,154 which are hereby incorporated by reference. One constant problem with these types of catalytic systems is the generation of fines during the catalytic process. These fines can eventually plug a catalytic bed. This leads to the necessity of replacing the catalytic bed thereby incurring additional cost.

SUMMARY OF THE INVENTION

It is an object of this invention to provide an improved process for the catalytic dimerization of olefins.

It is a further object of this invention to reduce fines in the catalytic dimerization of olefins.

In accordance with this invention, a process is provided which comprises: (a) contacting at least one olefinic compound with an alkali metal/alkali metal carbonate catalyst system at a temperature below the dimerization temperature range of the dimerization reaction; followed by (b) heating said olefinic compound and said alkali metal carbonate catalyst system to a temperature in said dimerization temperature range.

DETAILED DESCRIPTION OF THE INVENTION

Reactants for which this process is contemplated as useful are olefinic compounds which can (a) self-react, i.e., dimerize, to give useful products such as, for example, the self-reaction of propylene which gives 4-methyl-1-pentene; and/or (b) olefinic compounds which can react with other olefinic compounds, i.e., co-dimerize, to give useful products such as, for example, the co-dimerization of ethylene plus propylene gives 1-pentene, the co-dimerization of ethylene and 1-butene gives 3-methyl-1-pentene and so forth. As used herein, the term "dimerization" is intended to include "co-dimerization" as defined above.

Suitable dimerizable olefinic compounds are those compounds having from about 2 to about 30 carbon atoms and having at least one olefinic double bond. Exemplary compounds include, but are not limited to, acrylic and cyclic olefins such as, for example ethylene, propylene, 1-butene, 2-butene, isobutylene, 1-pentene, 2-pentene, 1-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, 3-ethyl-1-hexene, tetramethylethylene and the like; cyclopentene, cyclohexene, methylcyclopentene, methylcyclohexene, and the like an mixtures of any two or more thereof. Suitable co-dimerizable olefinic compounds are those compounds having from about 2 to about 30 carbon atoms, including all the compounds contemplated within the scope of "dimerizable" olefinic compounds as indicated above. The invention method is particularly appropriate in the conversion of propylene to 4-methyl-1-pentene.

Catalysts systems contemplated as useful in this invention are those having analkali metal carbonate support, at least one elemental alkali metal and optionally one or more of the following promoters: elemental copper, elemental cobalt, finely divided stainless steel, and mixtures of two or more thereof. It should be recognized, however, that the catalysts of the invention can contain additional components which do not adversely affect the catalyst performance, such as, for example, pigments, dyes, processing aids, inert fillers, binders and the like. Preferably the catalyst comprises a potassium carbonate support, potassium and one or more of the above-identified promotes. The proportion of promoter combined with the potassium carbonate support can vary appreciable, but generally, when a promoter is used, at least one weight percent of that promoter based on the total weight of the catalyst system will be employed.

This invention is contemplated to be useful when alkali metals such as lithium, sodium, potassium, rubidium and cesium are being used. While the proportion of alkali metal combined with the alkali metal carbonate support can vary appreciably, generally at least about one weight percent of alkali metal based on the total weight of the catalyst system will be employed. Similarly, potassium is the preferred alkali metal due to its ready availability as well as ease and safety in handling. The alkali metal carbonate support for the catalyst system may be prepared by any of several suitable means, including a "wet process" by mixing with water to a paste, drying and fractionating: or in a "melt process" by mixing with a non-acidic inorganic oxide support, heating, then cooling for treatment with metals. The dimerization catalyst system presently preferred in the process of this invention is a composition comprising about 4 to 8 percent by weight potassium metal, about 92 to 96 percent by weight potassium carbonate, and about 0 to 5 percent by weight promoter.

The dimerization reaction of this invention can be carried out using either batch or continuous types of operation. The dimerization process of this invention can be carried out by means of any apparatus whereby there is achieved contact of the catalyst with the dimerizable organic compound; suitable equipment such as, for example, autoclaves, tubular reactors and the like as well known in the PFS art can be employed. No special materials of construction are required so that steel, stainless steel, glass-lined reactors, or the like can be employed. The process is in no way limited to the use of a particular apparatus. The process of this invention can be carried out using a fixed catalyst bed, fluidized catalyst bed or moving catalyst bed. Presently the invention is considered most useful for dimerization with a fixed catalyst bed.

Any suitable dimerization reaction time may be used in the dimerization process. The dimerization reaction time will generally be in the range of about 0.05 seconds to about 10 minutes and will preferably be in the range of about 0.1 second to about 5 minutes. Any suitable catalytic dimerization temperature can be employed which provides the desired degree of catalytic activity in the dimerization reaction. The dimerization temperature will generally be in the range of about 50° C. to about 250° C./PFS, more preferably in the range of about 135° C. to about 170° C. and most preferably in the range of about 125° C. to 175° C.

The standard procedure for preparing the reactor for dimerization has been to heat the catalyst bed in the reactor to the dimerization temperature before the introduction of the dimerizable or codimerizable olefin. It has been discovered that by introducing the dimerizable or codimerizable olefin to the catalyst bed, at a temperature below the dimerization temperature range, prior to heating it to the dimerization temperature, the amount of fines generated is reduced. Specifically, the dimerizable or codimerizable olefin is introduced to the catalyst bed at a temperature below about 50° C. Preferably the dimerizable or codimerizable olefin is introduced to a catalyst bed when the temperature is between -50° and 45° C.; and most preferably the dimerizable or codimerizable olefin is introduced to the catalyst bed when the temperature is between 0° and 40° C.

The dimerization reaction can be carried out by contacting the dimerizable olefins with the catalyst system in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressures of about 1,000 to about 4,000 psig most preferred in order to achieve a good balance between reaction rate and minimizing equipment and operating costs necessitated by very high reaction pressures.

Any suitable feed rate for the organic feedstock can be utilized. The organic feedstock feed rate will generally be in the range of about 50 to about 5,000 volumes of gaseous feeds stock per volume of catalyst system per hour and will preferably be in the range of about 2 to about 8 kilograms of feedstock per kilogram of catalyst system per hour.

Because the reaction is carried out in the liquid or supercritical phase, solvents or diluents for the reactants can be used. Saturated aliphatic hydrocarbons, e.g., pentane, hexane, cyclohexane, dodecane; and aromatic compounds, preferably those without an alpha-hydrogen (which would be capable of undergoing alkylataion under the reaction conditions) such as benzene and chlorobenzene are suitable.

The contact time required for the dimerization reaction depends upon several factors such as, for example, the activity of the catalyst system, temperature, pressure, structure of the reactants employed, level of conversion desired, and the like. The length of time during which the dimerizable olefinic compounds are contacted with catalyst can vary conveniently between about 0.1 seconds and about 24 hours, although shorter and longer contact times can be employed. Preferably, times of about one minutes to about 5 hours are employed.

EXAMPLES

This example is provided to assist a person skilled in the art with understanding the invention. The particular reactants, conditions, and the like are illustrative only and are not meant to be construed as limiting the reasonable scope of this invention.

A series of runs were conducted to test the difference between reactor start up conditions and other various factors. The catalyst system used in all runs was a potassium-potassium carbonate catalyst. The catalyst came in two sizes, ⅛ of an inch particles and 8×12 mesh particles. The 8×12 mesh particles were ground and screened because the reactor used was only a ½" reactor with a 3/16" diameter thermocouple in its center, thereby allowing room for only a single ⅛" particle between the reactor wall and the thermocouple. In addition to the catalyst particles, 4 mm glass beads were added to the reactor to keep a constant volume. In the case of mixed materials the beads were mixed with the catalyst particles to give an even distribution throughout the catalyst bed. For layered materials, the catalyst was placed in a reactor in a single layer, with 4 mm glass beads packed in layers above and below the single catalyst layer. The 40 gram catalyst samples required 10 to 13 ml of glass beads (depending on the particle size and mixing) and the 10 gram samples required 49 ml of glass beads.

The hot startup method was to heat the reactor to the dimerization temperature under a nitrogen purge and then pump propylene into the reactor. The inventive reactor startup was to pump the propylene feed into the reactor prior to heating it from room temperature (about 20° C.) to the dimerization temperature.

In the table below fines were defined in two ways. For the runs where the catalyst particle size was ⅛", fines were defined as those particles which had a size equal to or smaller than 10 mesh. For those catalyst particles from the 8×12 mesh samples, fines were defined as those particles with a size equal to or less than 12 mesh. The amount of fines generated is reported as a weight percent based on the weight of the catalyst.

TABLE

| Reactor Start Up Method | Catalyst Particle Size | Reactor Temp. (C.) | Catalyst Sample Wt. (g) | Propylene Flow Rate (ml/min.) | Reactor Pres. (psi) | Catalyst Sample Structure | Fines Wt (%) |
|---|---|---|---|---|---|---|---|
| Inventive | ⅛" | 150 | 40 | 5 | 1600 | Mix | 4.7 |
| Inventive | ⅛" | 160 | 40 | 2 | 1600 | Layer | 2.85 |
| Hot | ⅛" | 150 | 40 | 2 | 800 | Layer | 15.23 |
| Inventive | ⅛" | 160 | 10 | 2 | 800 | Mix | 2.70 |
| Hot | ⅛" | 150 | 10 | 5 | 1600 | Layer | 8.00 |
| Hot | ⅛" | 160 | 10 | 5 | 800 | Mix | 10.40 |
| Inventive | 8 × 12 mesh | 160 | 10 | 5 | 1600 | Layer | 10.20 |
| Hot | 8 × 12 mesh | 160 | 40 | 5 | 800 | Layer | 13.03 |
| Inventive | 8 × 12 mesh | 150 | 40 | 5 | 800 | Mix | 8.08 |
| Hot | 8 × 12 mesh | 150 | 10 | 2 | 1600 | Mix | 22.80 |
| Hot | 8 × 12 mesh | 160 | 40 | 2 | 1600 | Mix | 7.90 |
| Inventive | 8 × 12 mesh | 150 | 10 | 2 | 800 | Layer | 13.20 |

As can be seen from the above data for the ⅛" catalyst particle size the amount of fines generated in the hot reactor startup method was about 11.2 weight percent whereas, in the inventive reactor startup method it was 3.4 weight percent. For the 8×12 mesh catalyst particle sizes, the amount of fines generated by the hot reactor startup method averaged about 14.6 weight percent whereas, for the inventive reactor startup method it averaged 10.5 weight percent.

That which is claimed is:

1. A dimerization comprising:
   (a) contacting at least one olefinic compound with an alkali metal/alkali metal carbonate catalyst system at a temperature below the dimerization temperature range of the dimerization reaction; followed by
   (b) heating said olefinic compound and said alkali metal carbonate catalyst system to a temperature in said dimerization temperature range.

2. A process according to claim 1 wherein said olefinic compound is selected from the group consisting of ethylene, propylene, 1-butene, 3-methyl-1-butene, 1-pentene, 3-methyl-1-pentene, 4-methyl-1-pentene, 1-hexene, 3-ethyl-1-hexene, and mixtures thereof.

3. A process according to claim 1 wherein said olefines compound is propylene.

4. A process according to claim 1 wherein said alkali metal in said alkali metal/alkali metal carbonate catalyst system is selected from the group consisting of lithium, sodium, potassium, rubidium, cesium, and mixtures thereof.

5. A process according to claim 1 wherein said alkali metal in said alkali metal/alkali metal carbonate catalyst system is potassium.

6. A process according to claim 1 wherein said alkali metal carbonate in said alkali metal/alkali metal carbonate catalyst system is selected from the group consisting of lithium carbonate, sodium carbonate, potassium carbonate, rubidium carbonate, cesium carbonate, an mixtures thereof.

7. A process according to claim 1 wherein said alkali metal carbonate in said alkali metal/alkali metal carbonate catalyst system is potassium carbonate.

8. A process according to claim 1 wherein said catalyst system of said alkali metal/alkali metal carbonate catalyst system further comprises at least one promoter selected from the group consisting of elemental copper, elemental cobalt, finely divided stainless steel, and mixtures thereof.

9. A process according to claim 1 wherein said dimerization temperature range is from about 50° C. to about 250° C.

10. A process comprising:
    (a) contacting propylene with a potassium/potassium carbonate catalyst system at a temperature below about 50° C.; followed by
    (b) heating said propylene and said potassium/potassium carbonate catalyst system to a temperature in the range of 125° C. to 175° C.

11. A process according to claim 10 further comprising recovering 4-methyl-1-pentene.

* * * * *

UNITED STATES PATENT AND TRADEMARK OFFICE
CERTIFICATE OF CORRECTION

PATENT NO. : 5,132,483
DATED : July 21, 1992
INVENTOR(S) : Paul F. Schubert

It is certified that error appears in the above-identified patent and that said Letters Patent is hereby corrected as shown below:

Claim 1, column 5, line 4, before "comprising" insert "process".

Claim 3, column 5, lines 19 & 20, delete "olefines" and insert ---olefinic---.

Signed and Sealed this

Second Day of November, 1993

Attest:

BRUCE LEHMAN

Attesting Officer   Commissioner of Patents and Trademarks